US012588808B2

(12) United States Patent (10) Patent No.: US 12,588,808 B2

Al-Qaisi (45) Date of Patent: Mar. 31, 2026

(54) IMAGING SYSTEMS WITH IMPROVED ACCURACY AND MEASUREMENTS

(71) Applicant: Aliph Medical LLC, Ladera Ranch, CA (US)

(72) Inventor: Muhammad Al-Qaisi, Ladera Ranch, CA (US)

(73) Assignee: Aliph Medical Inc., Lake Forest, CA (US)

( * ) Notice: Subject to any disclaimer, the term of this patent is extended or adjusted under 35 U.S.C. 154(b) by 990 days.

(21) Appl. No.: 17/516,217

(22) Filed: Nov. 1, 2021

(65) Prior Publication Data

US 2022/0167843 A1 Jun. 2, 2022

Related U.S. Application Data

(60) Provisional application No. 63/133,800, filed on Jan. 5, 2021, provisional application No. 63/118,752, filed on Nov. 27, 2020.

(51) Int. Cl.
*A61B 3/12* (2006.01)
*A61B 3/02* (2006.01)
(Continued)

(52) U.S. Cl.
CPC ................ *A61B 3/102* (2013.01); *A61B 3/12* (2013.01); *G06T 5/80* (2024.01); *G06T 2207/10101* (2013.01); *G06T 2207/30041* (2013.01)

(58) Field of Classification Search
CPC ......... A61B 3/02; A61B 3/102; A61B 3/1025; A61B 3/0075; A61B 3/113; A61B 3/1015; A61B 3/1225; A61B 3/024; A61B 3/005
(Continued)

(56) References Cited

U.S. PATENT DOCUMENTS 8,237,835 B1 8/2012 Muller
9,360,660 B2 6/2016 Yi et al.
(Continued)

FOREIGN PATENT DOCUMENTS

JP 2023553311 12/2023
KR 10-2023-0109665 7/2023
WO WO 2022/112882 6/2022

OTHER PUBLICATIONS

Search and Opinion in corresponding application PCT/IB2021/060105, issued Mar. 22, 2022 (15 pages).

(Continued)

*Primary Examiner* — Dawayne Pinkney
(74) *Attorney, Agent, or Firm* — Knobbe, Martens, Olson & Bear, LLP

(57) ABSTRACT

A system for providing accurate lateral mapping of images acquired via a scanning mechanism has a modulator synced to the imaging engine clock to generate image markers. The markers are then used to remove distortions and generate spatially-accurate mapping. A method of correcting image distortions by identifying the modulations and removing the distortions according to the spacing of the modulations. The system and the method applicable to ocular biometry and topography with the inclusion of an OCT arrangement to image the whole eye while the traversing the cornea and retina simultaneously, and with the inclusion of an on-axis imaging system to evaluate the quality of the ocular surface.

5 Claims, 14 Drawing Sheets

(51) Int. Cl.
  *A61B 3/024*    (2006.01)
  *A61B 3/10*     (2006.01)
  *G06T 5/80*     (2024.01)

(58) Field of Classification Search
  USPC ........ 351/206, 200, 205, 208–210, 221–223,
                351/245–246
  See application file for complete search history.

(56)       References Cited

U.S. PATENT DOCUMENTS

| | | |
|---|---|---|
| 2011/0222020 A1 | 9/2011 | Izatt et al. |
| 2012/0063660 A1* | 3/2012 | Imamura .............. A61B 5/0066 |
| | | 382/131 |
| 2021/0267799 A1* | 9/2021 | Neal ..................... A61B 3/101 |

OTHER PUBLICATIONS

Office Action received in EP Application No. 21 806 396.4-1001, issued May 20, 2025, 5 pages.
Office Action received in JP Application No. 2023-531535 with English Translation, issued Aug. 19, 2025, 5 pages.

\* cited by examiner

301

302

303

406

100

402

401

405

407

403

404

408

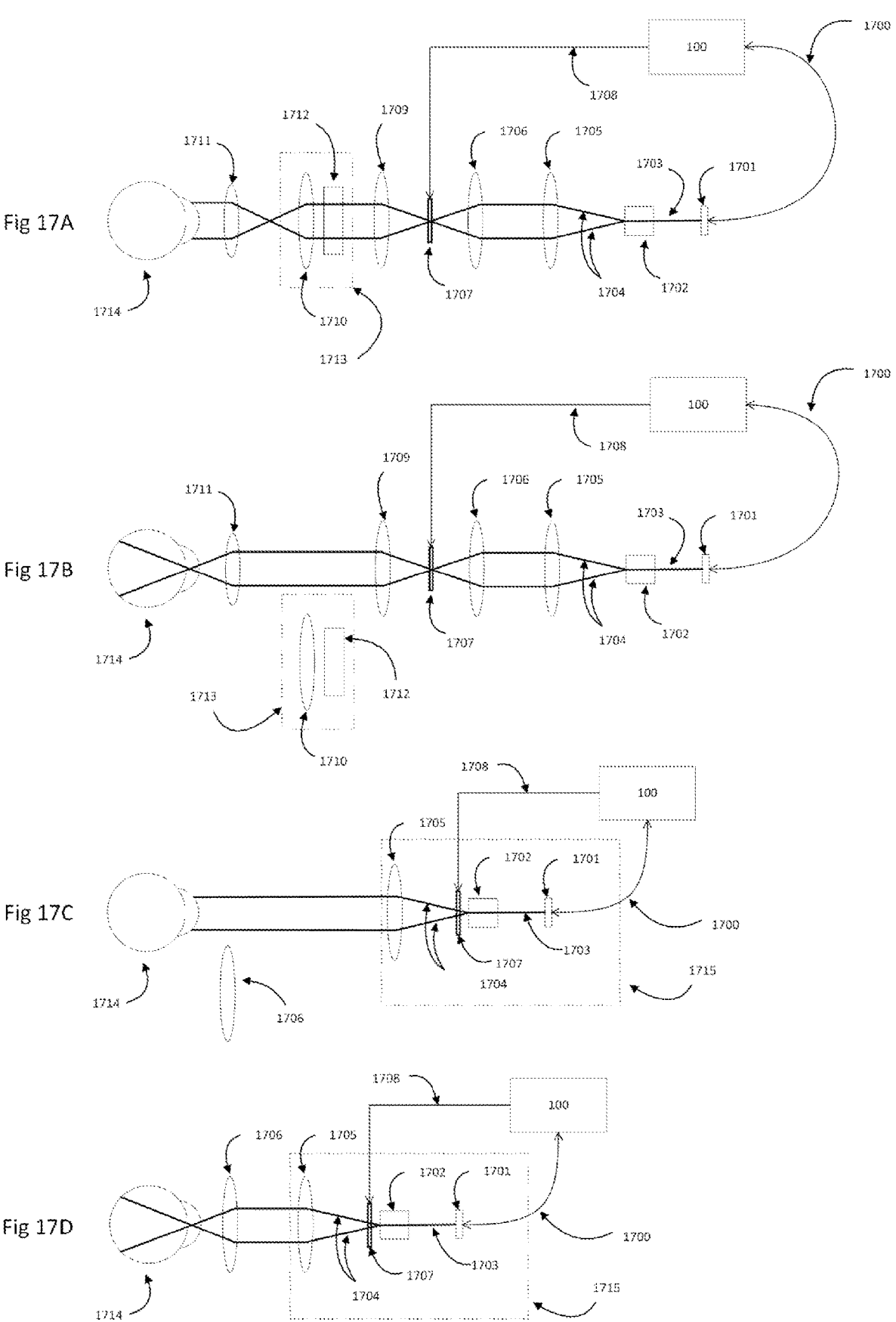

IMAGING SYSTEMS WITH IMPROVED ACCURACY AND MEASUREMENTS

CROSS-REFERENCE TO RELATED APPLICATION(S)

This application claims the benefit of priority under 35 U.S.C. §§ 120 and 119(e) of U.S. Provisional Application No. 63/133,800, filed Jan. 5, 2021, entitled "Spatiotemporal Modulation-Demodulation for Scanning Imaging Systems." This application also claims the benefit of priority under 35 U.S.C. §§ 120 and 119(e) of U.S. Provisional Application No. 63/118,752, filed Nov. 27, 2020, entitled "Imaging Systems with Improved Accuracy and Measurements." All of the foregoing are incorporated herein by reference in their entirety.

TECHNICAL FIELD

The present disclosure is directed to an approach that enables accurate mapping within optical coherence tomography imaging systems, and other scanner-based imaging systems.

The present disclosure is directed to adjustments on OCT images acquired using an OCT system to match outcomes calculated based on images acquired using another system with different performance characteristics.

The present disclosure is directed towards preferred scanning geometries for optical biometry.

BACKGROUND

Optical coherence tomography (OCT) is a widely-used imaging technique for medical, metrology and industrial applications. OCT technology provides a non-contact high-resolution imaging capability in turbid media. This interferometry-based technology provides superior sensitivity to minute intensities of light back-scattered or back-reflected from a sample. The technology provides a unique tool that visualizes topographies and subsurface features and structures down to micron-level resolutions.

The interferometric signal provides accurate spatial mapping in the depth (axial) dimension of the sample. The lateral dimensions of OCT scans depend on the scanning mechanisms of the light beam or the sample itself. Scanning can be horizontal and vertical, or circumferential or helical. Commercial OCT systems provide lower spatial accuracy along the lateral dimensions due to the utilization of mechanical scanners to scan the beam. Mechanical scanners cause distortions that are usually dynamic in nature and change over time. This limitation has caused OCT to fall short of its potential to map surfaces with nanometer-level accuracies. Lateral scan accuracy is expected to get more challenging as OCT system become faster which puts more demand on the mechanical scanners.

Achieving accurate OCT-based mapping system will eliminate the need for complementary mapping systems that are commonly combined with OCT, for example ocular placedo topographers. A reflection-based topographer like a placedo ring topographer is useful to study the quality of optical surfaces but it requires a large space to measure topography information accurately.

There is a need to provide accurate distortion-free OCT images in all dimensions. Addressing this need will serve several applications, like metrology of optical surfaces, accurate mapping of ocular surface to improve cataract and refractive surgeries, and many other applications. There is a need to have a complementary compact imaging system that can assist with the understanding of the health of optical surfaces of the object.

Often times OCT images are used to provide quantitative data using image analysis tools. For many conditions, this data can be tracked to monitor disease progression of patients over a period of years. The importance of having consistent progression monitoring requires that the image quality of the OCT system is not altered. This limits the ability of implementing significant image quality improvements of new systems due to potential change on measured quantities from an improved image of the same patient.

There is a need to provide transformations to the OCT images of improved systems that achieve similar quantitative analyses on the legacy systems without changes on the image analysis tools.

Optical biometry systems usually focus the light within the anterior segment causing a blurred spot on the fovea in most cases. Axial length is the most critical biometry measurement for IOL calculators and accurate measurement of the distance withing the foveal pit is therefore essential.

Capturing optical biometry data assumes the patient is fixated on a target aligned with the measurement system. Several approaches were proposed, some were implemented, to provide fixation based on the anterior segment of the eye, which does not accurately represent actual foveal fixation. Other approaches confirm the foveal fixation but they capture the foveal position after the actual measurement is taken, making the approach susceptible to errors due to eye movements.

There is a need to provide more accurate optical biometry systems that incorporates accurate and simultaneous fixation verification and correction.

SUMMARY: SPATIOTEMPORAL MODULATION-DEMODULATION SYSTEM

The present disclosure is directed to method and system for providing accurate lateral mapping of OCT imaging systems, single pixel imaging systems, or other systems that utilize scanners to generate multi-dimensional images. This approach is called Spatio-Temporal Modulation-Demodulation, or STMD in short.

In some embodiments, a system comprises an imaging engine and an object scanner. The object scanner is comprised of an optical setup with a scanning mechanism. The setup is tailored to scan the object and collect light back into the imaging engine. In the setup, an active modulator is inserted after the scanner and synced to the imaging engine clock to generate image markers. In this embodiment, a modulator is located after the scanner. The modulator is synced to an imaging engine clock to generate image markers, wherein the modulator is triggered at a rate that produces the image markers.

In some embodiments, the active modulator is triggered at a rate that causes a measurable marker on the image. For example, the modulator is clocked to produce at least one marker to at least one image element and further wherein the modulator is clocked at a rate that results in modulation that is an integer division of the imaging engine clock.

In some embodiments, the modulation causes at least one marker to at least one image element, for example a pixel or an A-line.

In some embodiments, the modulation rate is clocked to an integer divider of the master clock of the system.

In some embodiment the imaging engine can be an OCT A-line scanner comprised of a light source, a beam splitter and combiner configuration, a reference arrangement, at least one detector, processor, and display.

In some embodiments, the imaging engine can be a single-pixel camera or detector.

In some embodiments, the imaging system can be a line-scan camera.

In some embodiments, the imaging system can be a LiDAR (Light Detection and Ranging).

In some embodiments, the active modulator is placed in an optical plane approximately where the scanning mechanism is imaged.

In some embodiments, the active modulator is placed proximal to the scanning mechanism.

In some embodiments, the active modulator is placed distal to the optical elements of a scanning optical probe In some embodiments, the active modulator is placed anywhere in the optical path.

In some embodiments, the active modulator is placed after all optical components of the system to eliminate the need to do calibration of mechanical drifts of the scanners and optical distortions of the optical components.

In some embodiments, the active modulator can be an acousto-optic modulator, liquid crystal modulator, electro-optic modulator, piezoelectric device, galvanometer scanner, voicecoil, or another type of modulator.

In some embodiments, the active modulator can cause a phase delay on at least one image element.

In some embodiments, the active modulator can cause an amplitude change on at least one image element.

In some embodiments, the active modulator can cause a color change on at least one image element.

In some embodiments, the active modulator can cause a sharpness change or a fringe washout on the interferometric signal corresponding to at least one image element.

In some embodiments, the active modulator can cause speckle decorrelation to at least one image element.

In some embodiments, the active modulator can cause a change on image characteristic, like blurring, to at least one image element.

In some embodiments the active modulator can be replaced with a passive modulator.

In some embodiments, the passive modulator can incorporate spatial features that cause a phase, intensity, or another shift to an imaging event or more.

In some embodiments, the system is used to provide accurate mapping of ocular surfaces to help developing accurate IOL calculators or 3D eye model for planning of cataract and refractive surgeries.

In some embodiments, the system is used to provide accurate mapping of optical or precision surfaces.

In some embodiments, at least one feature is added to the object scanner to generate fiducials that can be used to calibrate the scale of the image to accurate spatial dimensions.

In some embodiments, at least one optical object is selected from the group consisting of: an optical fiber, a cylindrical object; a specular reflector, and a scatterer.

In some embodiments, the optical object is integrated into the modulator. In some embodiments, the optical object is comprised of the edges of the modulator.

In some embodiments, an optical path length of the fiducials is matched with an optical path length of a reference arm of the imaging engine.

In some embodiments, the fiducial is generated by optical interaction within the optical object without interference with the reference arm of the imaging system.

In some embodiments, the fiducials are inserted outside the field of view of the image.

SUMMARY: IMAGE PROCESSING

Image markers generated using the STMD method can be used to remove distortions on the image or final measurements based on the images using image processing.

In some embodiments, a method of correcting image distortions, comprises: placing image markers in at least one image of an object comprising surfaces, the image markers distributed along the surfaces, the image markers created by a modulator that produces modulations of elements in the image; identifying the modulations; and removing the distortions of individual images according to the spacing of the modulations in a horizontal dimension, the horizontal direction orthogonal to a z-direction of the imaging beam.

In some embodiments, z-modulations are removed from OCT A-lines by applying a shift along the z dimension.

In some embodiments, removing a phase delay applied to the image elements is accomplished by applying a phase shift on conjugate data which equates to a phase shift to image elements.

In some embodiments, the modulated elements are removed from the image.

In some embodiments, a second unmodulated image of the object without image marker pattern is received and distortion data calculated from the modulated image to the unmodulated image is applied to construct a corrected image.

In some embodiments, a method comprises receiving a second modulated image of the object the second set is modulated with a shifted image marker pattern from the pattern on the first set; identifying the shifted image markers; removing the distortions in images of the second images according the spacing of the modulations; and using unmodulated portions from the first set and the second image to construct a corrected image.

In some embodiments, a method may comprise one or more of the following: calculating topographic information from a plurality of corrected image; performing spatial scaling of the image based on prior knowledge scaling within a portion of the image with spatial data; and/or performing spatial scaling of the image based on measurements of a known object to produce image fiducials.

In some embodiments, image fiducials are produced by inserting at least an optical element with known width and height, or at least two elements with known spacing into an object scanner used to take the image.

In some embodiments, a method of correcting image distortions, comprises: placing image markers on a plurality of OCT images of an object comprising surfaces, the image markers created by a modulator that produces modulations of elements in the images; generating a topographic map from the images; identifying the modulations along the topographic projection; removing the distortions of the topographic map according to the spacing of the modulations.

In some embodiments, the topographic map is interpolated to fill the data in place of the modulated image elements.

In some embodiments, the z-modulations are removed by shifting OCT A-lines in the z dimension before a topographic map is calculated.

In some embodiments, performing spatial scaling of the image is based on measurements of a known object to produce image fiducials.

In some embodiments, image fiducials are produced by inserting at least an optical element with known width and height, or at least two elements with known spacing into an object scanner used to take the image.

In some embodiments, a method comprises receiving a second set of plurality of unmodulated image of the object without image marker pattern; and applying distortion data from the modulated topographic map to the unmodulated topographic map to construct a corrected map>

In some embodiments, for OCT images, baseline curvature can be removed from the image. Numerical derivative of the image can be taken to identify the indexes of the image markers.

In some embodiments, phase delay applied to the A-lines can be removed by shifting the A-line data, or, for more accurate results, applying a phase shift by applying an index shift on the spectral data which equates to a phase shift to the spatial A-line data.

In some embodiments, A-lines with image markers can be used to correct distortions but the A-lines themselves can be removed from the image.

In some embodiments, another image of the same object with a shifted image marker pattern is acquired. At least one image is processed to identify the image markers and the data of the indexes of marked zones of image is then replaced with data from the unmarked zones of the other image.

In some embodiments, accurate spatial scaling of the image can be achieved based on prior knowledge scaling within a portion of the image with reliable spatial data.

In some embodiments, accurate spatial scaling of the image can be achieved based on measurements of a known object before or after the scan.

In some embodiments, accurate spatial scaling of the image can be achieved based on at least two image fiducials based on at least one object placed in the object scanner.

In some embodiments, the image fiducials can be achieved by inserting an optical element with a known width to the object scanner, or two elements with knows spacing.

In some embodiments, the optical elements can be automatically removable from the optical path.

In some embodiments, a sequence of images is acquired to record at least one image of the object with image markers and fiducials, and an unmarked image of the object. Image analysis of the image markers and fiducials can be applied to provide distortion correction information applicable to the unmarked image.

In some embodiments, the image data can be interpolated based on the image marker indexes to yield uniform and accurate spacing of the a-lines or image components.

In some embodiments, the final analysis data, for example topography data, can be interpolated based on the image marker indexes to yield accurate topographic information.

SUMMARY: OPTICAL SURFACE QUALITY EVALUATION

The disclosure is directed to an invention to complement an OCT imaging system with a compact pattern-based reflection system to study the quality of the optical surfaces.

Reflections of light patterns captured by a camera is a useful tool to evaluate the corneal topography and break down of tear film on the corneal surface. This approach to measure corneal topography requires a relatively large angle between the incident rays on the cornea and the reflected rays. As the tear film breaks up on the corneal surface, the quality of the reflections degrades and a correlation between the tear film quality and the quality of the captured images can be established.

Because STMD provides accurate mapping of the ocular surfaces, there is no need to use reflection patterns to provide topography information. The difference between the angles of incidence and reflections can therefore be significantly reduced or even eliminated and the arrangement of the illumination pattern and the camera can sufficiently provide tear film analysis using a compact system.

In some embodiments, an imaging system comprises: an imaging engine; a scanner system comprising a scanner; a modulator located after the scanner, the modulator synced to an imaging engine clock to generate image markers, wherein the modulator is triggered at a rate that produces the image markers; and a pattern-based reflection system where the illumination pattern and imaging camera are comprised of approximately identical optical cone angles, and the pattern-based reflection system coupled to the scanner system via a dichroic combiner.

In some embodiments, the imaging engine is an OCT system, and the dichroic combiner is located in an OCT imaging path.

In some embodiments, the pattern-based reflection system further comprises: a light source, the light source generating a pattern that is merged with the OCT imaging path.

In some embodiments, the system comprises a camera, wherein the camera images the pattern after the pattern is reflected off of a corneal surface.

In some embodiments, the reflected pattern is registered to compensate for eye movements.

In some embodiments, the system comprises a processor programmed to perform a differential analysis of the reflected pattern to analyze ocular surfaces.

In some embodiments, the camera is also used to guide the imaging system to align to the eye.

In some embodiments, a light source is masked to generate a pattern that gets merged in the optical path of the objective scanner using a dichroic beam combiner. The light gets projected on the corneal surface. The reflected light gets collected through the same dichroic beam combiner and imaged through a camera.

In some embodiments, the light source can be a comprised of one or more light source, preferably light emitting diodes.

In some embodiments, the light source can generate a pattern by sequentially illuminating different areas at different times.

In some embodiments, subsequent reflection images from the corneal surface get registered to compensate for movements then a differential analysis can be applied to establish an analysis of the health of ocular surfaces.

In some embodiments, the same camera can be used to guide the ophthalmic system to align to the eye.

SUMMARY: ROBUST BIOMETRY WITH FIXATION EVALUATION

The disclosure is directed towards optical biometry scan configurations that provide accurate measurement of the axial length at foveal pit for all ocular powers of the eye, and provides accurate fixation verification simultaneous to the biometry scan.

Ocular biometers typically utilize an optical beam that is focused within the anterior chamber of the eye. Because the numerical aperture of the beam is typically small, the spot size on the retina is not expanded a lot. Variables like different eye lengths and visual acuity, however, result in significantly different spot size on the retina for different patients. The axial length measurement is best when the center of the foveal pit is interrogated, and a larger spot size results in measuring an average of a larger zone and lower signal intensity and integrity. Both result in reduced accuracy of the most critical parameter of ocular biometry.

Said beam is usually not scanned in A-line biometers, or scanned in approximately a paraxial fashion to provide more coverage of the anterior segment surfaces. Neither of these configurations lend itself to real-time foveal pit visualization for fixation verification or correction. For a paraxial scan on eyes with 0 diopter correction the scanned beams will always converge on the fovea.

For eye with diopter correction the beams will converge posterior or anterior to the foveal surface causing the interrogation spot to scan over the fovea for the different A-lines, resulting in averaging over a nonuniform area. Similar effect is caused by other semi-paraxial scans. When the data is analyzed, A-lines are averaged which causes an error due to blurring, or only one A-line is used for the analysis which makes the system measurement prone to error due to noise.

It is preferable to scan the optical biometry beam to scan with a pivot point within the pupil, or approximately anterior or posterior to the pupil. It is preferable to have the beam focused on the retina to provide ocular biometry measurements. This configuration provides crisp cross-sectional image of the retina.

In some embodiments, an ocular biometry system comprises: an OCT engine producing an imaging beam; a scanner that directs the imaging beam at an eye; a focus assembly that focuses the beam approximately on the retina, a first set of lenses in a path of the imaging beam that scans the imaging beam at a pivot point located in an anterior chamber of the eye at a plane containing a pupil of the eye or parallel plane located just anterior or posterior the pupil; the imaging beams pivots at the pivot point to image the whole eye while simultaneously scanning a line on the retina and the cornea of the eye.

In some embodiments, an optical assembly is insertable into the path of the imaging beam that pivots the imaging beam at a point anterior or posterior to the cornea in order for the imaging beam to simultaneously scan over structures of the cornea and the lens.

In some embodiments, the optical assembly comprises an assembly lens and a delay element. In some embodiments, the delay element is selected such that an optical path length difference when the optical assembly is in the path of the imaging beam and when the assembly is out of the imaging beam path is reduced or eliminated.

In some embodiments, the first set of lenses comprises a first telescope and a second telescope, each telescope comprising two lenses, and wherein the optical assembly is inserted between the lenses of the second telescope.

In some embodiments, the system further comprises a modulator in the path of the imaging beam after the beam scanner.

In some embodiments, an ocular biometry system comprises: an OCT engine producing an imaging beam; a scanner that directs the imaging beam at an eye; a first lens in a path of the imaging beam that focuses and scans the imaging beam to allow for imaging of structures in the anterior chamber; a second lens insertable into the path of the imaging beam that pivots the imaging beam at a point anterior or posterior to the cornea in order for the imaging beam to simultaneously scan over structures of the cornea and the lens; wherein when the second lens is in the path of the imaging beam, the beam is approximately focused on the retina; and wherein when the second lens is in the path of the imaging beam, the beams pivots at the pivot point to image the whole eye while simultaneously scanning a line on the retina and the cornea of the eye.

In some embodiments, a modulator is located in the path of the imaging beam

In some embodiments, the foveal pit is visualized and the visualization of the pit with the cross-sectional scan of the whole eye, combined with the camera image of the front of the eye, can be used to identify the optical axis and visual axes of the eye, and calculate angle kappa and angle lambda. It can be also used for reliable fixation verification, and for calculating accurate biometry measurements even in the absence of proper fixation.

In some embodiment, multiple cross-sectional scans at different positions can be captured to generate volumetric biometry and information on ocular orientation.

In some embodiments, the optical system withing the object scanner is adjusted to compensate for ocular power and eye length to ensure the beam is focused on the retina.

In some embodiment, the said adjustment is based on prior knowledge of the ocular power, visual acuity, or eye length.

In some embodiments, the focus adjustment is varied during the cross-sectional scan according to astigmatism or higher order aberrations.

In some embodiment, the pivot position within the lens or anterior chamber combined with scan area on the retina are utilized to calculate the effective lens position.

In some embodiment, a delay line in the object scanner or reference arm is utilized to compensate for eye length.

In some embodiments, a speckle analysis is applied to the image to accurately locate the scan pivot point.

In some embodiment, the said preferred scan geometry is combined simultaneously or sequentially with another scan geometry dedicated for the anterior segment.

BRIEF DESCRIPTION OF THE DRAWINGS

The accompanying drawings illustrate exemplary implementations of the systems and approaches disclosed herein and, together with the text, serve to explain the principles of the present disclosure.

FIGS. 17a and 17b show an arrangement that performs paraxial scanning of the eye in one instance, and scans with pivoting beams in the pupil plane in another instance. Switching is achieved by removing optics from the optical path with consideration of a specific optical path length difference between the two states.

FIGS. 17c and 17d show an arrangement that performs paraxial scanning of the eye in one instance, and scans with pivoting beams in the pupil plane in another instance. Switching is achieved by removing optics from the optical path with ability to move the optical setup to adjust to a specific optical path-length difference between the two states.

DETAILED DESCRIPTION

Figure 1:
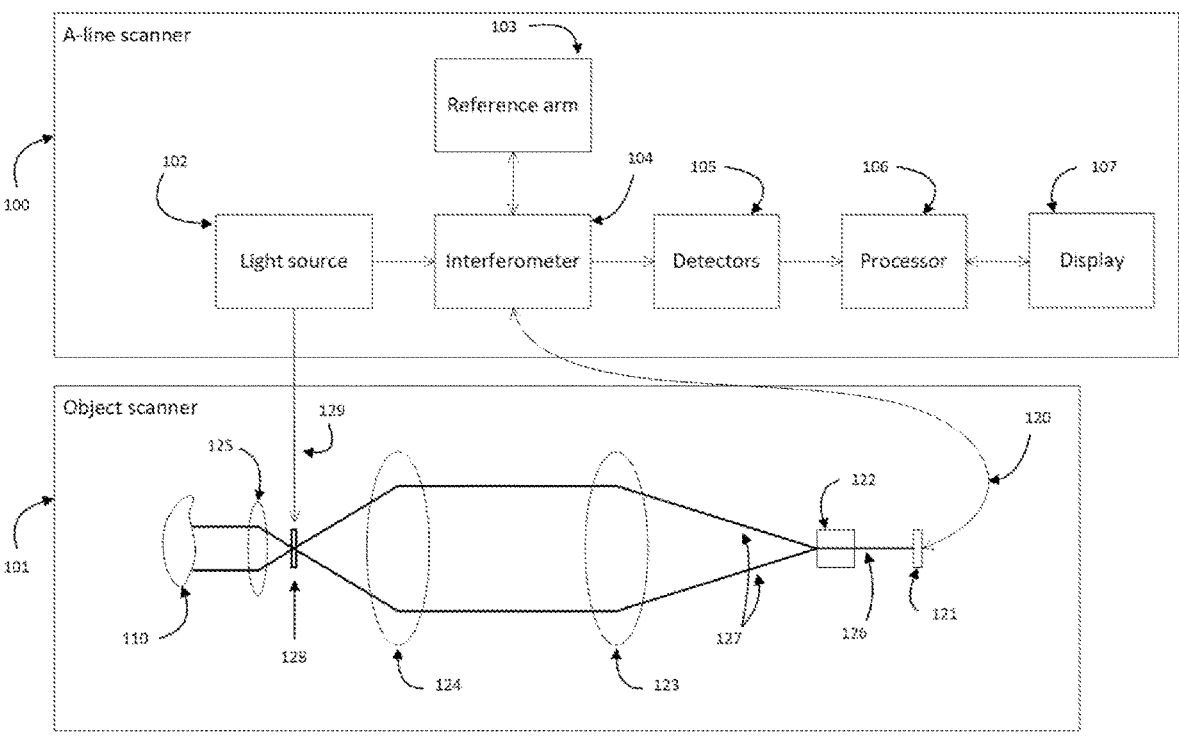
FIG. 1 shows an example embodiment of a system for performing optical coherence tomography to accurately map the surfaces of an object by incorporating a Spatio-Temporal modulation (STMD) scheme.

For the purposes of promoting an understanding of the principles of the disclosure, reference will now be made to the implementations illustrated in the drawings, and specific language will be used to describe the same. It will nevertheless be understood that no limitation of the scope of the disclosure is intended. Any alterations and further modifications to the described systems, devices, instruments, methods, and any further application of the principles of the present disclosure are fully contemplated as would normally occur to one skilled in the art to which the disclosure relates. In particular, the features, components, and/or steps described with respect to one implementation may be combined with the features, components, and/or steps described with respect to other implementations of the disclosure. For simplicity, in some instances the same reference numbers are used throughout the drawings to refer to the same or like parts.

FIG. 1 illustrates an example of systems that encode modulations on the 2-dimensional or 3-dimensional OCT images for the purpose of accurate correction of static and dynamic distortions. The A-line scanner 100 directs light through the object scanner 101 optics to the object or tissue to be examined. OCT imaging may be performed for a surface or set surfaces, such as a precision component like an optical surface. Posterior segment imaging can also be performed, for example to examine the retina, and/or for anterior segment imaging, for example to examine the lens and/or cornea.

FIG. 1 show a system for performing accurate mapping of OCT data in three dimensions using STMD. The A-line scanner 100 comprises a light source 102, an interferometer 104, a reference arm 103, detectors 105, processor 106, and display 107. Sample light from the interferometer is directed into the object scanner 101 where a set of optical components scan the light beam on the horizontal and vertical dimensions of object 110. Light enters the object scanner 101 through a waveguide 120 and an optical component 121 to shape the beam typically in a collimated beam 126. The beam is scanned by means of scanner (or scanning mechanism) 122 with a maximum angular range shown by the marginal rays 127. The telescope comprised of lenses 123 and 124 images the scanning component plane onto the modulator 128 that is synced to the light source 102, in case of a swept-source OCT, via connection 129. The optical beam is finally scanned on the object 110 via the objective lens 125. The spacing between 123 and 124 can be changed to adjust the beam convergence or divergence on the object 110.

Figure 2:
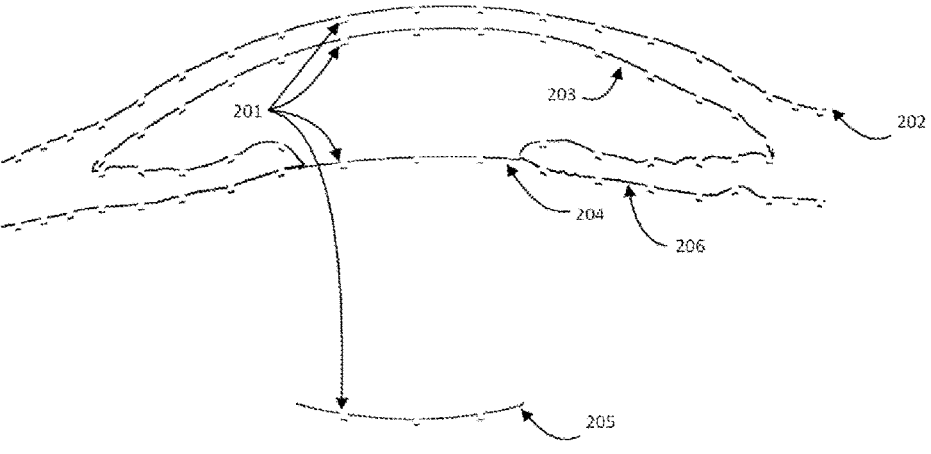
FIG. 2 shows a sketch representing an anterior-segment OCT image showing the STMD modulations as z-modulations.

In one example, to achieve the required modulations for STMD, a high-speed modulator 128 is incorporated after the scanner (or scanning mechanism) 122. The modulator 128 is timed with A-line trigger to mark one or more A-lines out of every N number of A-lines. When the modulator 128 is capable of applying a significant phase shift in the z-direction, the modulations will be observed as z-shifted A-lines as shown in FIG. 2. The shifts 201 are called z-modulations. Because the modulation is performed in fixed temporal intervals whereas the scanners are not moving at a constant speed, the spacing between the image markers can be used to correct for the distortions caused by non-linearities in the lateral scans, resulting in distortion-free images and measurements. In one example, the z-shift is at least equal to one pixel to enable the image processing algorithm to detect the positions of the modulated A-lines. Image modulations can be removed to produce a clean image. The z-modulations can be undone by reversing the shift amount in the digital domain.

FIG. 2 shows a representation of an OCT cross-sectional image of the anterior segment of the eye showing the anterior cornea 202, posterior cornea 203, anterior lens 204, posterior lens 205, and iris 206. The example of FIG. 2 shows A-lines with phase shift due to z-modulations. The markers 201 can be used to correct for non-linearity and inaccuracies of the scanning mechanism.

Figures 3, 4:
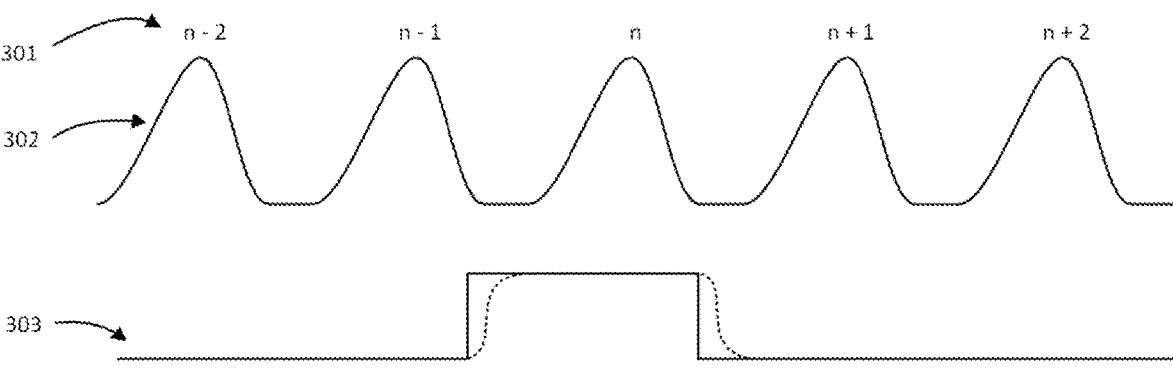
FIG. 3 the timing diagram to achieve such modulations on a SSOCT.
FIG. 4 shows an example optical setup to achieve z-modulations using n rapidly-actuated optical delay line assembly.

FIG. 3 shows one example of a timing scheme for applying the modulation for a single A-line. In order to achieve this modulation, the modulator 128 is driven by a step function 303 to apply a delay on specific A-lines. In this case, the response time of the modulator 128 is sufficient to perform the transition between the subsequent A-lines. Most Swept-Source (SS) OCT lasers operate at about a 70% duty cycle and switching can occur during the 30% off time. 301 shows the A-line ID number. 302 shows the laser sweep profile vs time. 303 shows the modulation command in solid lines, and the time response of the modulator in dotted lines.

The interval of the modulation represents the total number of A-lines per cycle (modulated+unmodulated A-lines). The duty cycle of the modulation represents the ratio of modulated A-lines to the interval. In this example, in order to detect positional distortions on the image two conditions are achieved. The first condition is that the interval is significantly smaller than the total number of A-lines per scan to provide sufficient sampling of the scan dynamics. The second condition is that the duty cycle is significantly larger than ½ to avoid averaging during the modulation. In experimentation, it has been found that best outcomes are therefore achieved when modulations on the OCT image are represented by a single A-line modulated at a time. A duty cycle of ½ will not carry distortion information because the spacing between modulated A-lines represented by a single A-line does not provide recoverable information about the lateral speed of the scan.

Experimentation has found that a direct phase modulation approach with Lithium Niobate crystal is stable and repeatable. In this example, a Lithium Niobate crystal implementation is limited to small aperture size, and situations where the polarization-dependance of the shift is not a consideration.

In another example, phase modulation using Acousto-Optic (AO) crystals is a workable way to create z-modulations. In this case, a first-order diffraction beam is picked from the AO phase-shifter with modulation frequency $f_o$ that is sufficient to separate the first order from the zeroth-order diffraction. Since OCT depth information is modulated based on frequency, applying this constant frequency shift means that the zero-delay position now coincides to $f_o$ and not f=0. If $f_o$ is equal to $f_N/2$, where $f_N$ is the Nyquist frequency for the analog to digital conversion process, the zero-delay position will be in the middle of the imaging range. To achieve the frequency shift, the modulation frequency of the first-order diffraction can be changed to $f_o+\delta f$ for the period in which the A-lines are to be shifted. The baseline frequency modulation can be kept if needed. If not desired, it can be demodulated during the A-line reconstruction process, or another AO modulator can be placed either in the sample or reference arm to eliminate the $f_o$ modulation and limit it to $\delta f$.

FIG. 4 shows an example in which an alternative modulation scheme can be achieved by placing a mirror on a piezoelectric device (mechanism 407) in the optical path to achieve desired modulation parameters. In this example, the A-line scanner 100 (also referred to as the OCT engine) illuminates the optical setup via the collimator 401. The beam is scanned on the object 408 via the scanner mechanism 405 and the lenses 402, 403, and 404. The mechanism 407 is comprised of a folding reflector setup mounted on a piezo-actuator that is actuated to modulate the A-lines. The modulation is synced with the A-line sweeps via A-line trigger 406.

It is also possible to perform intensity modulation (i-modulation) instead of phase modulation. The advantage of this approach is that implementing intensity modulation is simpler. Intensity modulators operate at high-speeds and the modulation can be applicable to single A-lines without impacting the preceding or succeeding A-lines. An example of an intensity modulator is a solid-state modulator, such as an AO operated in intensity modulating-mode. In this example, the absence of content in the modulated A-lines can help identify and correct the positional errors in the scanners, see, e.g., FIG. 6. The information in the modulated A-lines is unrecoverable from the same image. The impact is manageable via one of the following two approaches. The first approach is to record two subsequent scans by repeating the same scan pattern. One of the scans will be with i-modulation and the other will not be modulated. The distortion information calculated based on the modulated scan can be applied to the second scan to produce a distortion-free image or map. The second approach is applicable to topography applications where multi-dimensional surfaces fit to the segmented OCT surfaces; the sparse absence of data points that corresponds to the blanked A-lines may not be found to influence the results.

Figure 5:
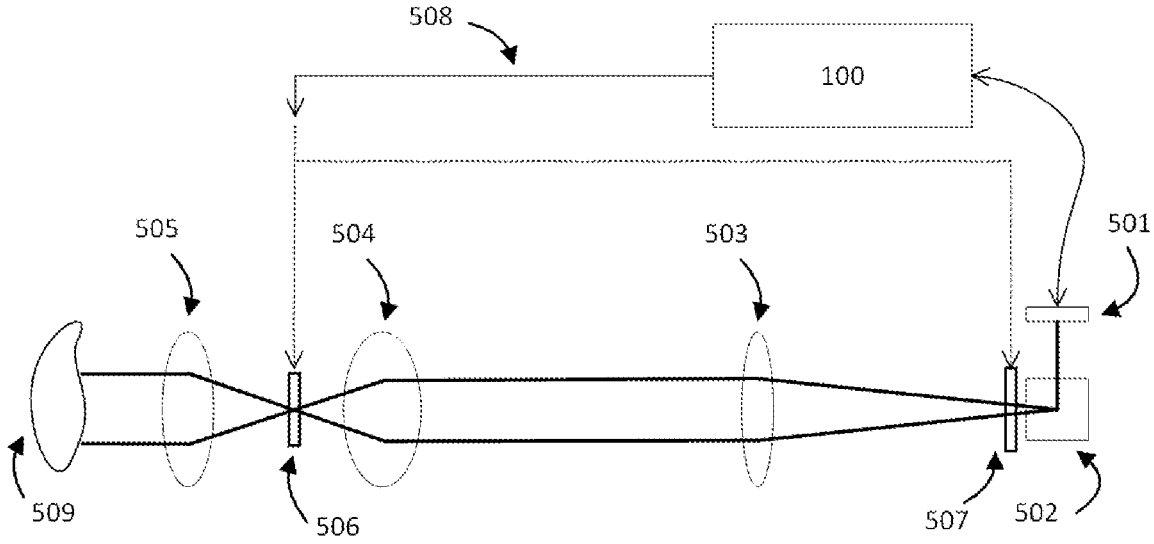
FIG. 5 shows an STMD-based OCT system with two possible placements of the modulator; one in the scanner conjugate, and the other proximal to the scanner.

In another example, intensity modulation can be performed by incorporating an intensity modulator in the optical path. FIG. 5 illustrates a setup where the OCT engine or A-line scanner 100 illuminates the optical setup via the collimator 501. The beam is scanned on the object 509 via the scanner mechanism 502 and the lenses 503, 504, and 505. In this example, only one of the two modulators 506 or 507 shown in the figure is needed. The modulation performed by the modulator 506, 507 is synced with the A-line sweeps via A-line trigger 508. In one example, modulator 507 is located between scanner 502 and lens 503. In this example, modulator 507 is coupled to OCT engine 100 via A-line trigger 508. In another example, modulator 506 is located between lens 504 and lens 505. In this example, modulator 506 is coupled to OCT engine 100 via A-line trigger 508.

In one example implementation, intensity modulation can be performed by means of inserting an AO modulator in the optical path at either of the positions 506 or 507, or by simply actuating a mirror, such as that described in the dynamic optical delay of FIG. 4, during the A-line to blur its content (in the case of SSOCT) or blank it by washing the spectral fringes (in case of Spectral-Domain OCT). The step response demand of the dynamic optical delay in this case is significantly lower than that required for z-modulation. For example, a modulation amplitude of π-2π is sufficient, and the rise and fall times are faster. In this example, this approach works in two modes: z-modulation at lower OCT rates, and i-modulation at higher rates.

Figure 6:
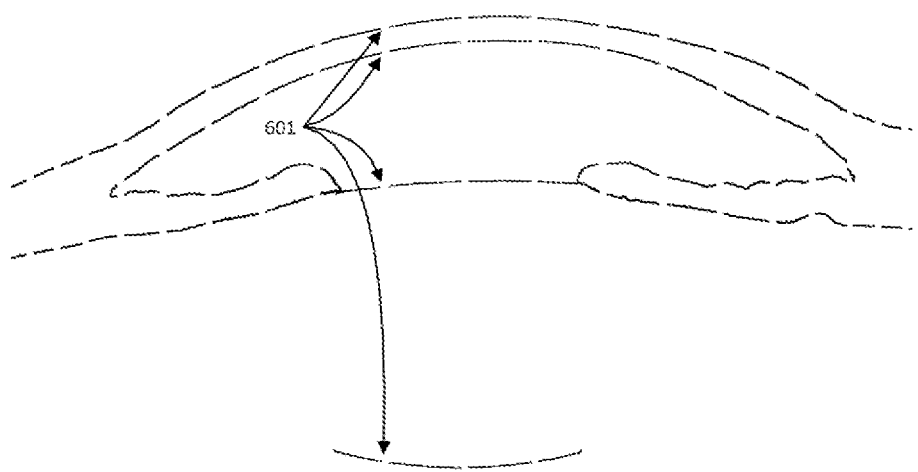
FIG. 6 shows a sketch representing an anterior-segment OCT image showing the STMD modulations as i-modulations.

FIG. 6 shows an example where i-modulation markers 601 are created by intensity modulation rather than phase modulation. Markers 601 may be located on each imaged surface.

Figure 7A:
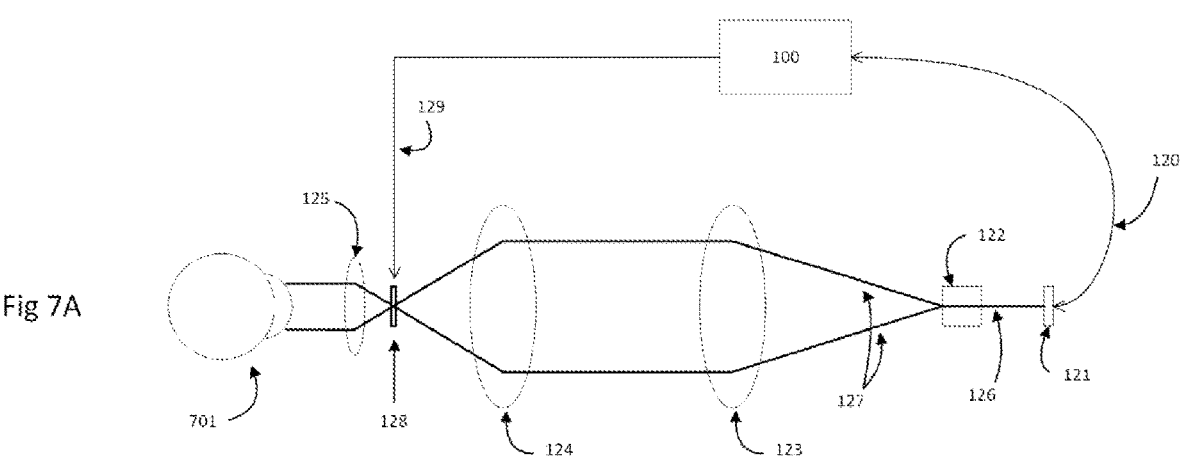
FIG. 7a shows the system in FIG. 1 where the object to be imaged is an eye. The optics is scanning the beam on the eye in approximately paraxial scans. The modulator is placed in approximately in the scanner's conjugate plane.

FIG. 7a shows the same setup as in FIG. 1 where the scanned object is an eye 701 or any part or segment of eye 701.

Figure 7B:
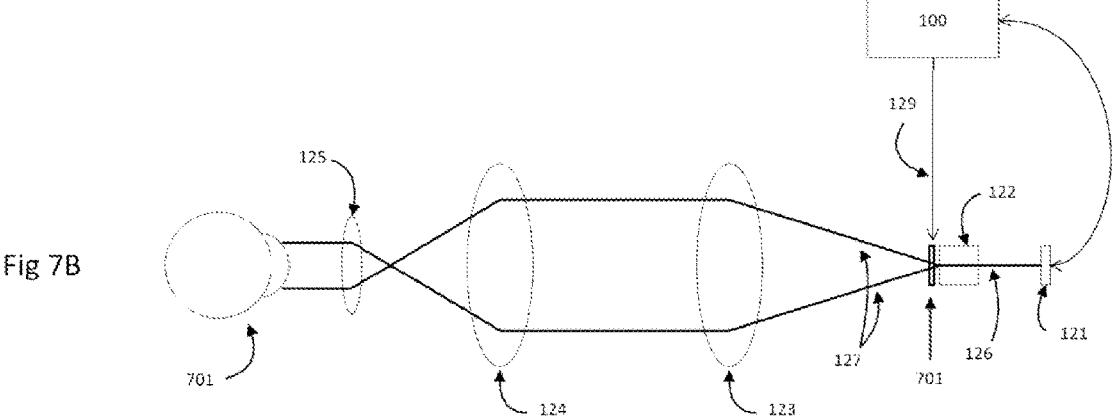
FIG. 7b shows the system in FIG. 1 where the object to be imaged is an eye. The optics is scanning the beam on the eye in approximately paraxial scans on the anterior segment. The modulator is placed in proximal to the scanners.

FIG. 7b shows the same configuration as FIGS. 1 and 7a with different placement of the modulator 701 to be proximal to the scanning component. In this example, modulator 701 is located adjacent to scanner (or scanning mechanism) 122. This placement of the modulator 701 allows for more freedom of the downstream optical design. For example, lens 125, 124, and 123 can be removed. In this example, modulator 701 has a wider acceptance angle and larger aperture than the modulator 128 in the setup of FIG. 7a.

Figure 7C:
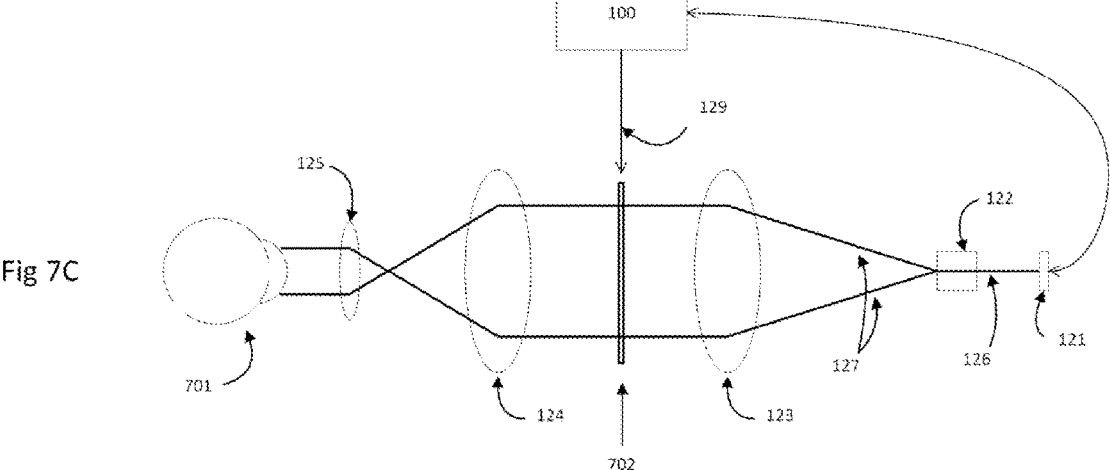
FIG. 7c shows the system in FIG. 1 where the object to be imaged is an eye. The optics is scanning the beam on the eye in approximately paraxial scans on the anterior segment. The large-area modulator is placed in withing the free-space of telescope assembly.

FIG. 7c shows the same configuration as FIG. 7a and FIG. 7b with different placement of the modulator 702 which is placed between lenses 123 and 124. In this example, modulator 702 is a wide-area modulator. This placement of the modulator 702 allows for more freedom of the downstream optical design. For example, lens 125 and 124 can be removed. In this example, the configuration reduces requirements on acceptance angle of the modulator. Large area modulators such as liquid crystal modulators, typically have slower response time, but are sufficient for the purposes here.

Figure 8A:
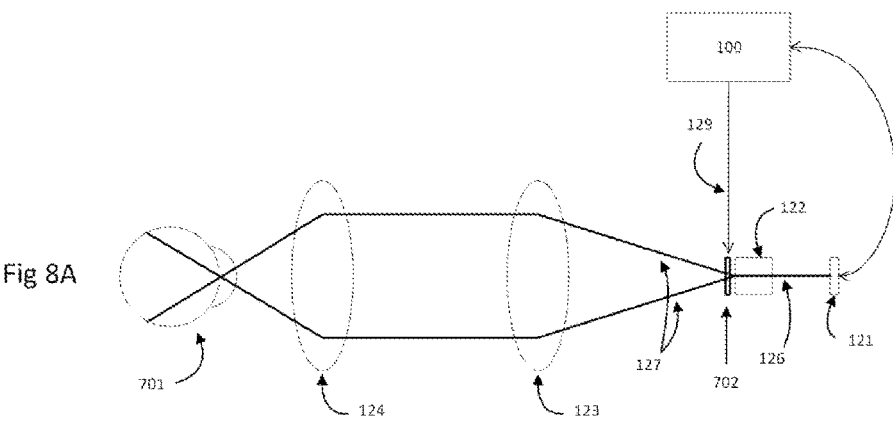
FIG. 8a shows a system similar to FIG. 7b with modification to scan the beam where it converges on the anterior segment and approximately pivots in the pupil plane causing the beam to scan on the posterior eye. The modulator is placed in proximal to the scanners.

FIG. 8a shows an example configuration that enables OCT imaging of the posterior segment of the eye 701. The example of FIG. 8a is similar to that of FIG. 7b. In this example, the OCT engine or A-line scanner 100 illuminates the scanning mechanism (or scanner) 122 via the collimator 121. The modulator 702 is located proximal to scanning mechanism (or scanner) 122. The telescope comprised of lens 123 and lens 124 pivots the beam approximately around the pupil plane of the eye (the plane located in the anterior chamber of the eye and containing the pupil). The spacing between lens 123 and lens 124 can be changed to adjust the focus on the retinal tissue. The example of FIG. 8a is suitable for imaging posterior eye structures such as the retina and retinal layers as well as objects or structures in the posterior segment of the eye.

Figure 8B:
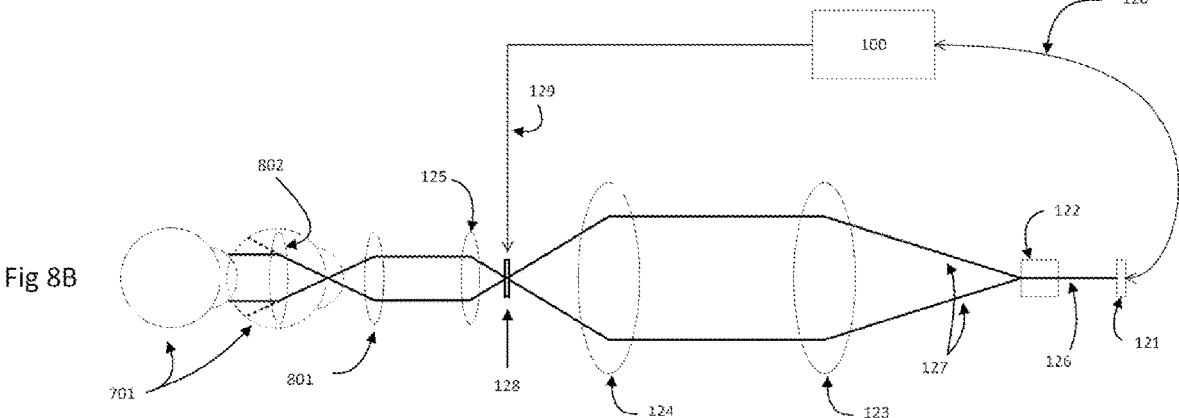
FIG. 8b shows a system that can scan the eye with an approximately paraxial beam at the anterior segment at some instances, and switch to approximately pivoting the in the pupil to scan the posterior segment. The optical delay difference between the anterior segment plane and posterior segment place of the two modes, respectively, is minimized. The modulator is placed in the scanners' conjugate plane.

FIG. 8b shows an example configuration where the OCT engine or A-line scanner 100 illuminates the modulator 128 via the collimator 121, scanning mechanism (or scanner) 122, and telescope comprised of lens 123 and lens 124. The modulated light beam then scans the posterior segment of the eye 701 via lenses 125 and 801, or the anterior segment of the said eye by adding the lens 802. In this example, lens 802 is a movable objective lens that enables the optical setup to scan either the anterior segment (when the lens 802 is out of the optical path) or the posterior segment of the eye (when the lens 802 is in the optical path). In another example, lens 802 is in the optical path when imaging the anterior segment and out of the optical path when imaging the anterior segment. This configuration provides the flexibility of switching between anterior and posterior eye scans and reduces the aperture requirements for the modulator 128 which achieves higher speeds.

Figure 8C:
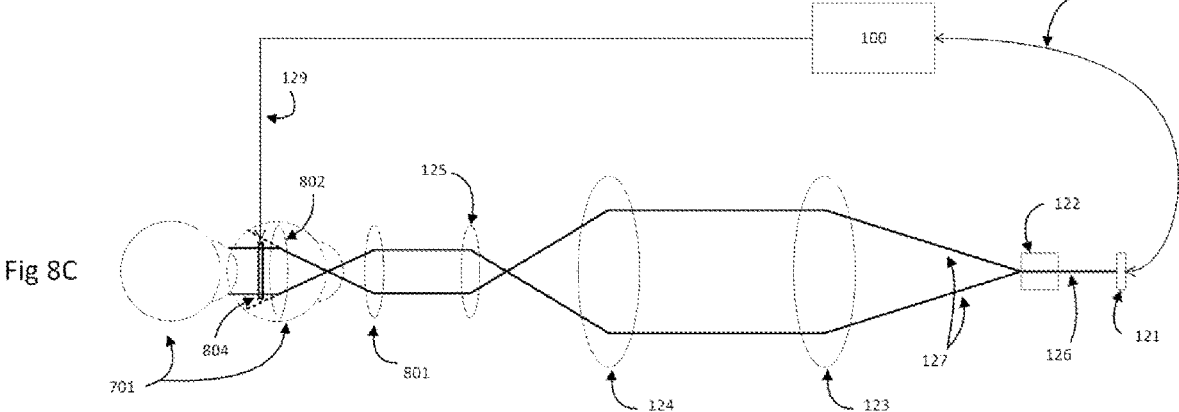
FIG. 8c shows a system that can scan the eye with an approximately paraxial beam at the anterior segment at some instances, and switch to approximately pivoting the in the pupil to scan the posterior segment. The optical delay difference between the anterior segment plane and posterior segment place of the two modes, respectively, is minimized. The modulator is placed after the last optic in the paraxial scan mode, and removed from the optical path in the pupil pivoting scan mode.

FIG. 8c shows an example configuration where the OCT engine or A-line scanner 100 illuminates the modulator 804 via the collimator 121, scanning mechanism 122, and lenses 123, 124, 125, 801 and 802. In this example, the modulated light beam scans the anterior segment of the eye 701 directly. Because the modulator 804 is placed as the last optical element of the system, this configuration provides the ability to compensate all static and dynamic system distortions in the system. To scan the posterior eye, both lens 802 and modulator 804 are removed from the optical path. In this case, STMD is not applied to the posterior segment scans of the eye. In this example, the modulator 804 is incorporated into an assembly containing lens 802.

Figure 9:
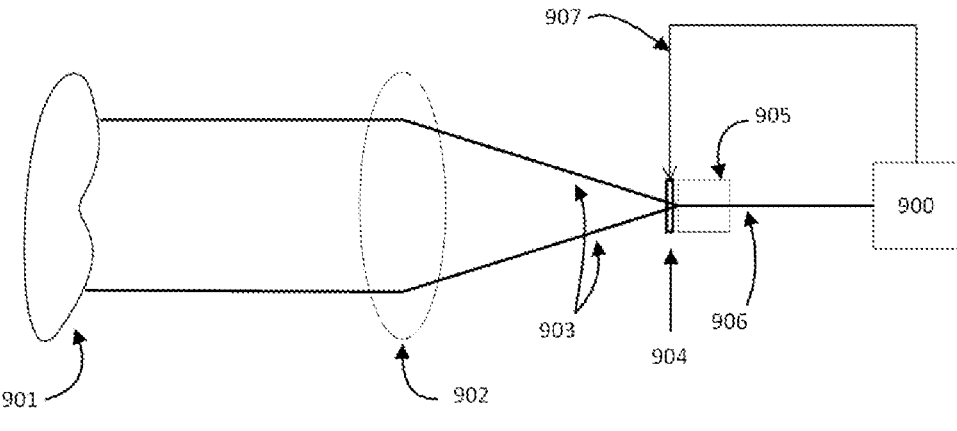
FIG. 9 shows a simplified scanning optical setup that can be used for single-pixel imaging of objects.

FIG. 9 shows an example of a scanning mechanism and an imaging engine 900. In this example, imaging engine 900 may be OCT or another technology, for example a single-pixel camera. For single-pixel camera-based imaging system, one portion of the object 901 is imaged by the lens 902 on the scanning mechanism 905 via the modulator 904. The beam then propagates to the camera 900. To image another potion of the object, the scanning mechanism is moved to collect light from that portion. A plurality of image points is collected to generate an image as the scanning mechanism 905 continues to move. The angular extent of the scanned beams is shown as 903. The modulator 904 is synched via line 907 to the imaging engine 900 and is triggered in to generate i-modulations on the image. The modulations are used to correct distortions in the image.

Figure 10:
FIG. 10 shows an example algorithm workflow to reconstruct spatially-corrected information from images with z-modulations.

FIG. 10 shows an example of a method for modulated images or topographies. The input to the method is an STMD image where z-modulations carry distortion information, the output is an image where distortions are removed. The modulated image 1001 is processed in 1002 to remove baseline curvature if needed, for example, to approximately flatten the anterior surface of the cornea. The derivative applied in 1003 is taken along the horizontal direction of one or more surfaces. The outcome of the derivative is used in 1004 and 1006 to identify the start and end indexes 1005 and 1007 of the modulation events.

z-modulations are removed in 1008 where the indexes calculated in 1005 and 1007 define the first and last A-lines to be shifted in a given interval. The shift is applied by applying a sub-pixel phase shift to the z-modulated A-lines. The shift can be achieved by oversampling, or by processing the spectral A-line by offsetting the wavelength index. This will result in precise phase shifting on the A-line. The offset amount can be pre-calculated based on prior knowledge of the system or based on minimizing the difference between pixels.

If the goal is to remove distortions caused by the scanning mechanism from an individual image, for example a B-scan, an interpolation step is applied in 1010 to the image 1009 to rescale the horizontal dimension according to the indexes in 1005 and 1007. The output is a corrected image 1011 with no scanning distortions.

If the goal is to remove distortions caused by the scanning mechanism from a volume of data, for example a topography map, the topography is calculated from a plurality of images 1009. The topography is then corrected in 1013 by interpolating the three-dimensional information according to the indexes in 1005 and 1007. The output is a corrected topography 1014 with no scan distortions.

Figure 11:
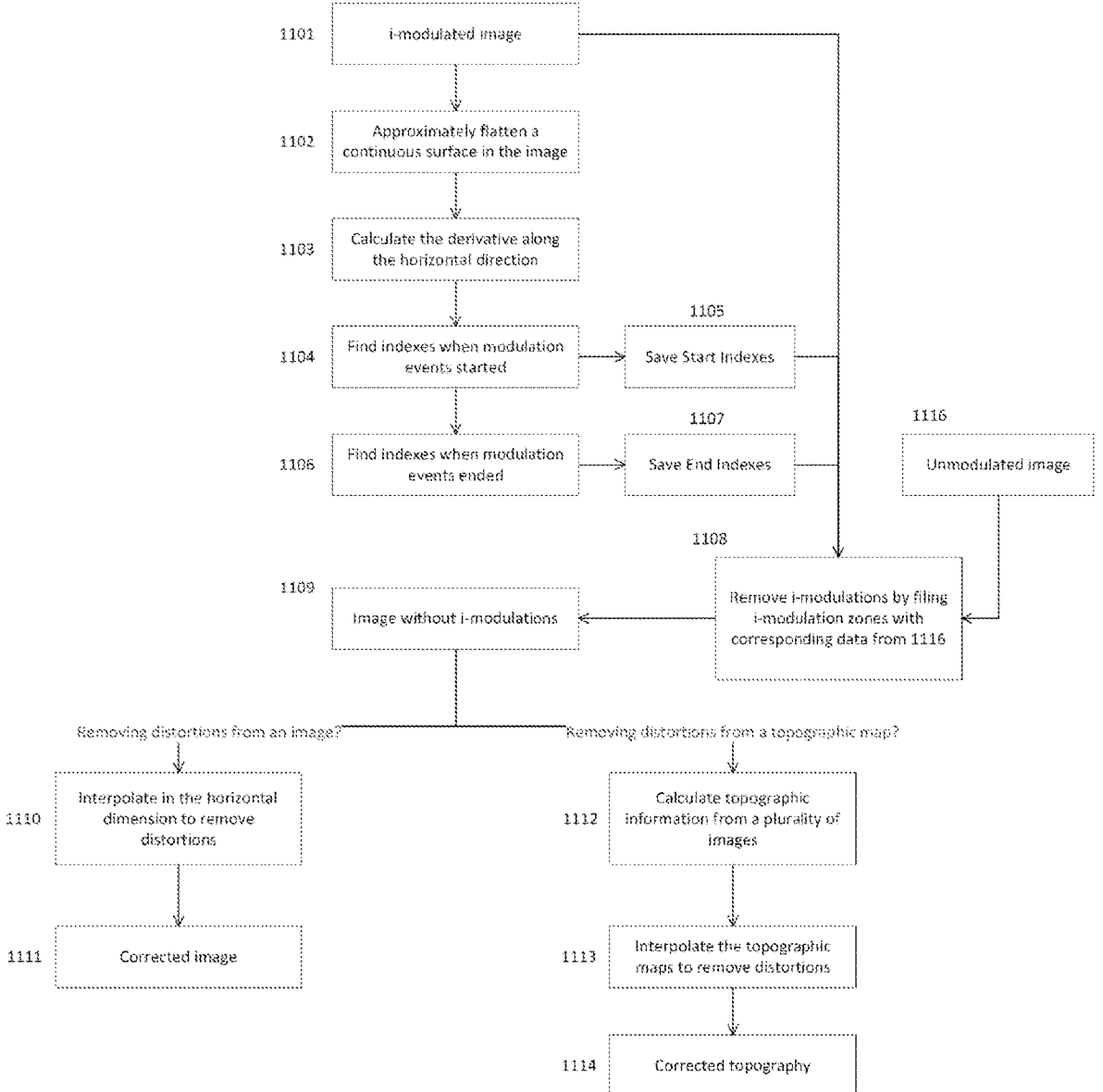
FIG. 11 shows an example algorithm workflow to reconstruct spatially-corrected information from images with i-modulations.

FIG. 11 shows an example of a method to process modulated images or topographies. The input to the algorithm is an STMD image where i-modulations carry distortion information, the output is an image where distortions are removed. The modulated image 1101 is processed in

1102 to remove baseline curvature if needed, for example, to approximately flatten the anterior surface of the cornea. The derivative applied in 1103 is taken along the horizontal direction of one surface or more. The outcome of the derivative is used in 1104 and 1106 to identify the start and end indexes 1105 and 1107 of the modulation events.

i-modulations are removed in 1108 where the indexes calculated in 1105 and 1107 define the first and last A-lines to be replaced within a given interval by A-lines from an unmodulated image 1109 that was acquired subsequently to image 1101.

If the goal is to remove distortions caused by the scanning mechanism from an individual image, for example a B-scan, an interpolation step is applied in 1110 to the image 1109 to rescale the horizontal dimension according to the indexes in 1105 and 1107. The output is a corrected image 1111 with no scanning distortions.

If the goal is to remove distortions caused by the scanning mechanism from a volume of data, for example a topography map, the topography is calculated from a plurality of images 1109. The topography is then corrected in 1113 by interpolating the three-dimensional information according to the indexes in 1105 and 1107. The output is a corrected topography 1114 with no scanning distortions.

Figure 12:
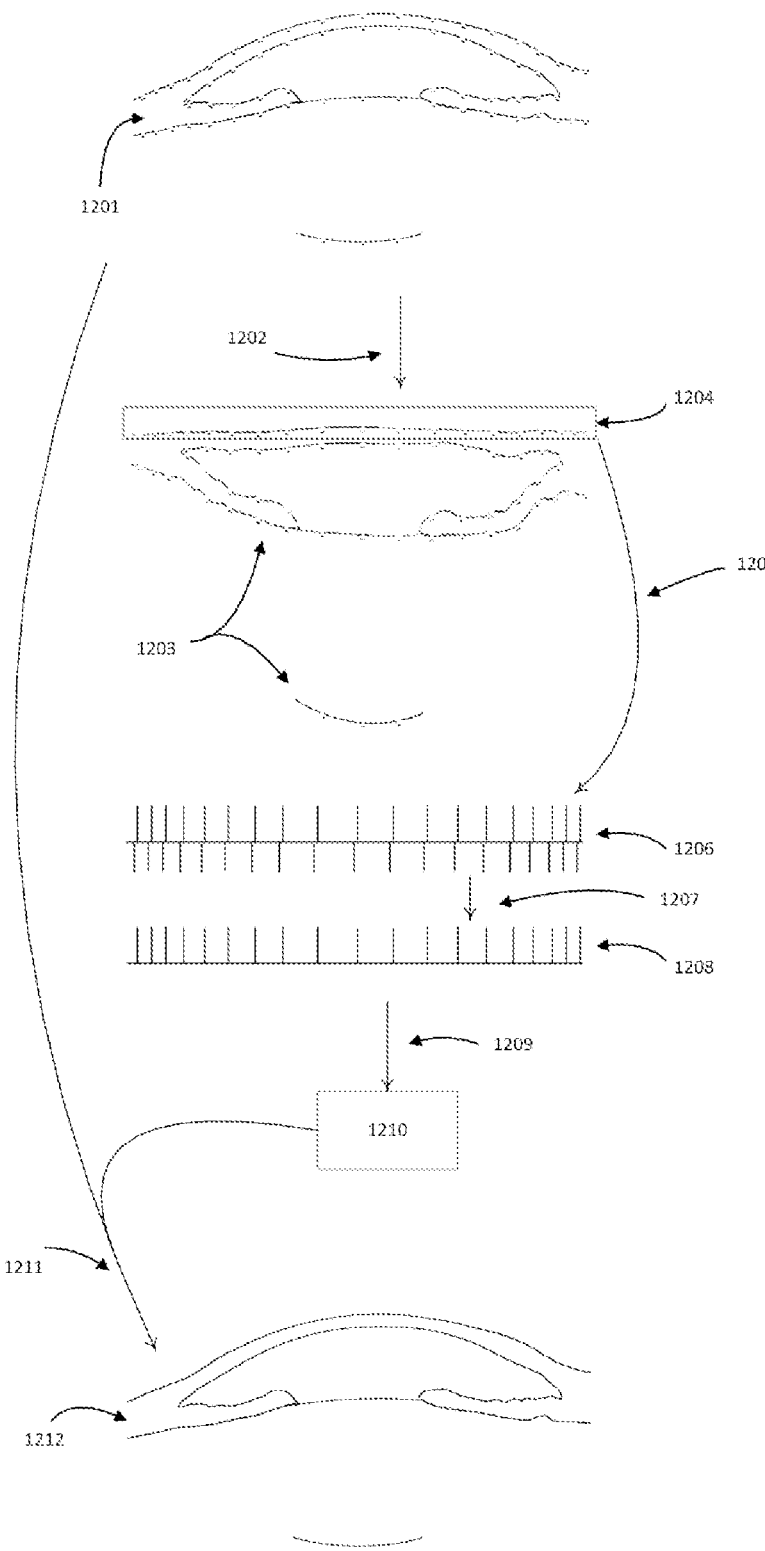
FIG. 12 illustrates major steps in the algorithm that reconstructs spatially-corrected information from images with z-modulations as shown in FIG. 10.

FIG. 12 shows an example of the steps taken to remove modulations and distortions from an OCT image of the anterior segment. Most of the curvature of the anterior corneal surface of the z-modulated image 1201 is removed in step 1202. Step 1202 can be performed by removing the curvature of average corneas, or by detecting the curvature on the anterior surface of this specific image after smoothing the surface, then shifting the A-lines according to the information in the curvature. The image 1203 is the same as 1201 after removing the curvature in 1201. The envelope 1204 shows that the anterior corneal surface is now isolated from the rest of the image. In step 1205, a derivative along the horizontal direction is applied to the enveloped portion of the image 1204. The outcome of the derivative is shown in 1206 where negative and positive spikes correspond to the start and end of each modulation event, respectively. To select the positive spikes only as shown in 1208, the negative spikes are removed in step 1207 by eliminating all values below the horizontal line. The indexes of the spikes are identified in step 1209 and a vector of the indexes is stored in 1210. In step 1211 the indexes are applied to remove the z-modulations and interpolate the image to remove distortions and produce the corrected image 1212.

The image in 1212 is distortion-corrected for all lateral distortions caused parts before the modulator that was used to modulate the image. This includes static distortions from the optics, and static and dynamic distortions from the scanning mechanism. Static distortions of the optics downstream of the modulator and fan distortion can be calibrated out. In this example, the surface that was used for distortion correction, i.e. the anterior corneal surface in the example in FIG. 12, is considered as the reference when other distortion corrections are applied.

Scaling of the STMD-corrected image to the proper lateral scale can be achieved by calibrating the image using a known target. Since scanning mechanism usually have non-linear response with respect to velocity, different scan patterns may require different scaling. To ensure accurate scaling is applied regardless of the scan pattern, spatial fiducial marks can be incorporated in the image. Because the image distortion is removed as described earlier, two points are enough to scale the image accurately. This is done by adding markers that represent additional image fiducials based on physical features with precise dimensions. The markers can be used to provide a reference to use for accurate scaling.

For an OCT system, the fiducials can be generated by imaging two optical objects in the sample arm through the interference of their signal with the reference arm. This will require matching the optical pathlengths of the fiducials with the reference arm either by shortening the reference arm or extending the optical path towards the fiducials in the sample path.

To ensure the fiducials will not interfere with the image, they need to be inserted outside of the field of view of the image and get imaged by increasing the scan range of the scanner before, after, or during the imaging process. Alternatively, they can be placed on a setup that can be actuated to insert or remove them from the optical path.

Fiducial markers can be specular reflectors or scatterers. Scatterers require less alignment which is desired specifically for actuated fiducials.

They can alternatively be integrated within the modulator by itching, laser marking, or simply by imaging the edges of the modulator.

Thin cylindrical objects, like optical fibers, can be used as fiducial markers. Because the fibers are thin it is easy to generate an autocorrelation signal within them that can be easily visible on the OCT image. Because autocorrelation in the sample path does not require interference with light from the reference arm, this approach eliminates the requirement for adjusting the optical pathlength between the sample and reference arms. These features will be visible near zero delay through a depth proportional to the optical path between the correlating features within the sample arm.

Figure 18A:
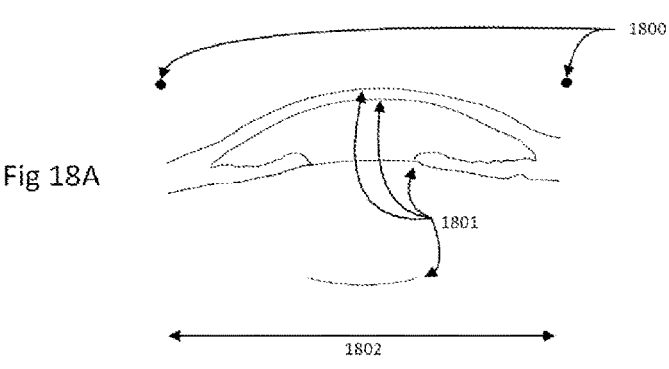
FIG. 18a shows an example OCT image of the anterior segment layers of the eye with fiducial marks placed outside of the field of view of interest.

FIG. 18a shows an example OCT image of the anterior segment layers of the eye 1801 with fiducial marks 1800 placed outside of the field of view of interest 1802.

In the case of swept-source OCT, autocorrelation is usually suppressed by balanced detection. The suppression is, however, limited to around 30 dB. In this case, the autocorrelation intensity should exceed balanced-detection suppression to be visible.

Features generating autocorrelation fiducials can be also generated by creating features within the modulator itself or within an optical element that can be possibly bonded to the modulator. For example, a ring comprised of two surfaces with, about a 0.25 mm spacing, can be created via altering the index of refraction of optical media that is bonded to the modulator. A ring of cloud scatterers can be alternatively utilized. The ring feature should be written outside of the imaging field of view if the feature is static in the optical path. It can be within the field of view if the feature is removable from the optical path.

Figure 18B:
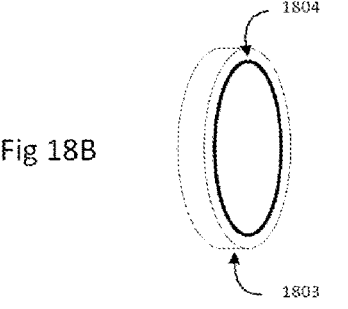
FIG. 18b shows a ring feature which is part of an element.

FIG. 18b shows an example where the ring feature 1804 is part of element 1803, which can be the modulator itself or a separate optical element.

Figure 18C:
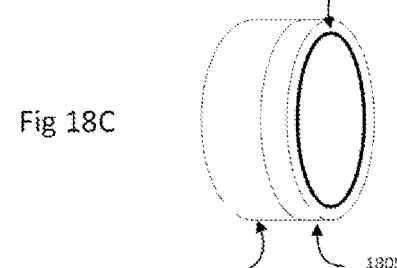
FIG. 18c shows a ring feature that is part of an optical element that is bonded, attached, or placed proximal to the modulator.

FIG. 18c shows an example where the ring feature 1804 is part of an optical element 1805 that is bonded, attached, or placed proximal to the modulator 1806.

In another example, four-point feature marks can be used instead of the rings. The marks should be written outside of the imaging field of view if the feature is static in the optical path. It can be within the field of view if the feature is removable from the optical path.

Figure 18D:
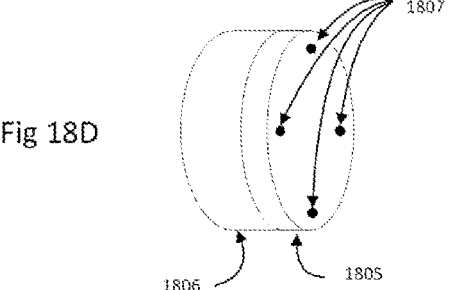
FIG. 18d shows a four-point feature that is part of an optical element.

FIG. 18d shows an example where a four-point feature 1807 is part of an optical element 1805 that is bonded, attached, or placed proximal to the modulator 1806.

Figure 18E:
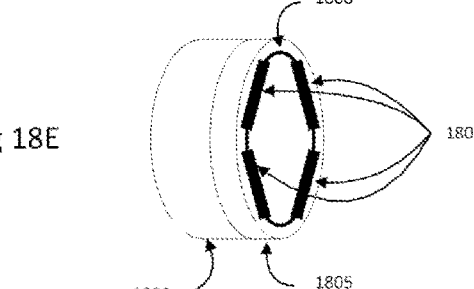
FIG. 18e shows an optical fiber attached to an optical element adjacent to a modulator.

FIG. 18e shows an example where a feature comprised by an optical fiber 1808 is attached to an optical element 1805 that is bonded, attached, or placed proximal to the modulator 1806. The fiber is attached to optical element 1805 via a mount 1809 that does not interfere with the B-scan field of view and leaves at least four segments of the fiber exposed for optical interrogation.

Biometry & Topography with Optical Surface Quality Evaluation

Figure 13:
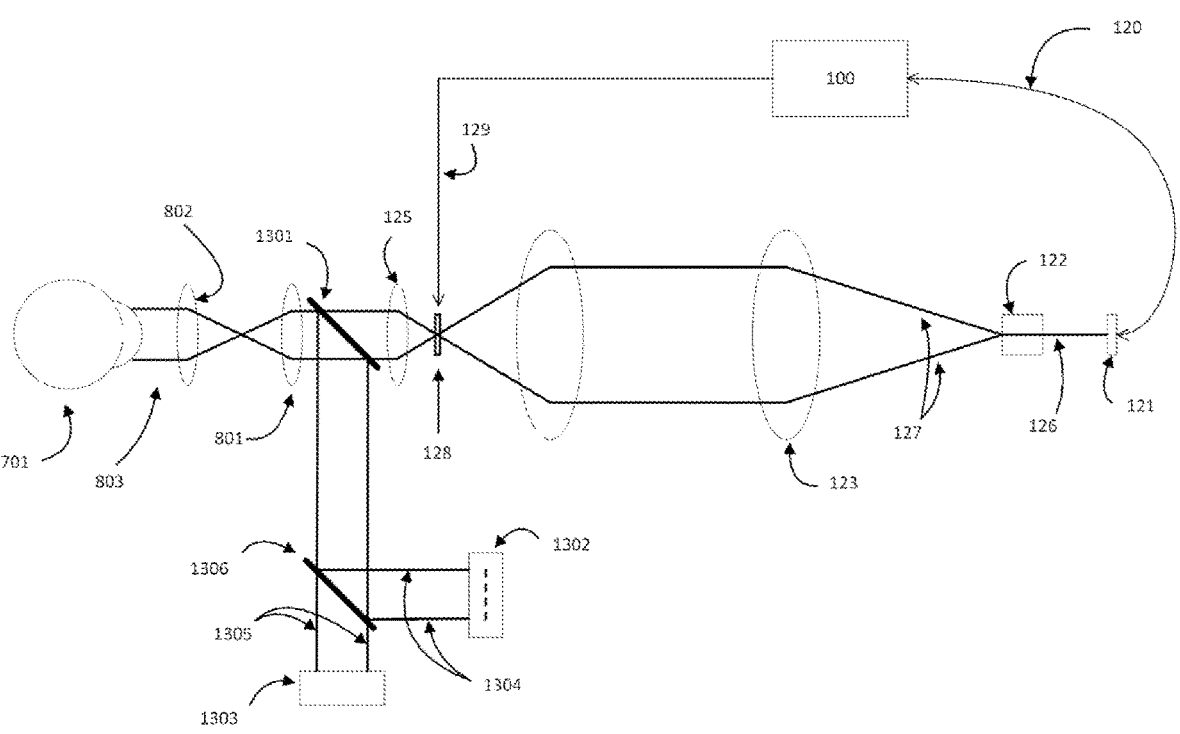
FIG. 13 shows an STMD-based OCT system with a reflection-based image system that projects an image on the corneal surface to study the health of the ocular surfaces.

FIG. 13 shows an example of an OCT-based STMD system used for accurate mapping of ocular surface similar to the system presented in FIG. 1, FIG. 7a, and FIG. 8a combined with a compact reflection-based arrangement to evaluate the health of the corneal surface and the tear film of the eye. In this setup, STMD allows OCT to provide accurate topography maps of the corneal and lens surfaces. Topography maps represent the shape of a particular surface, for example anterior corneal surface, including sphericity, toricity, and high-order aberrations. The reflection-based arrangement in FIG. 13 provides information about the tear-film health because reflections of the light from the anterior cornea are more sensitive to disruptions of the tear film than OCT. Because topography information is not extracted from the reflection-based arrangement, the setup does not require a large angle between the illumination and imaging beams on the cornea like placido topographer, allowing to build the system in a compact setup.

The arrangement in FIG. 13 is comprised of a pattern 1302 that is generated that has dark areas and bright areas. The illumination beam 1304 from the pattern is directed via a beam splitter 1306 then injected in the OCT path via the dichroic combiner 1301. The pattern is then projected on the anterior surface of the cornea and the image of the pattern on the cornea is directed back out of the OCT path via 1301. The collected beam is directed via 1306 to capture the beam 1305 on the camera 1303. The illumination pattern 1302 can be comprised of features that are a function of time as well as space, or a combination of both.

Reflection-based patterns that can be utilized in this arrangement can be comprised of concentric rings, an array of spots, or a grid of lines. Other patterns or shapes may also be used. To avoid aliasing of discrete spots on the cornea, temporal modulations could be used.

Figure 14:
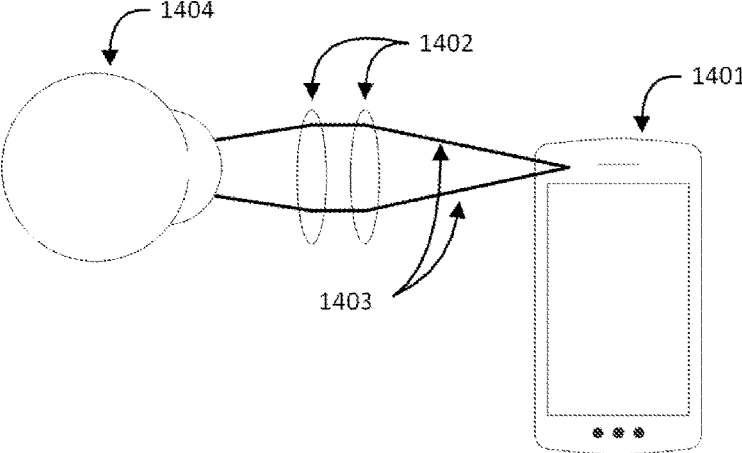
FIG. 14 shows mobile-device based setup to study the health of the ocular surfaces.

FIG. 14 shows a setup that utilizes a mobile device with temporally-modulated illumination spots to evaluate corneal topography and tear-film breakup characteristics. Mobile phone hardware for face recognition and for LiDAR include arrays of illuminated spots that get imaged using a camera system adjacent to the illumination array. Distortions of the illumination pattern get translated into 3-dimensional maps. The field of illumination and field of view of the native optical system of mobile phones (or iPhones) is fairly large and the resolution is on the order of a millimeter which is not sufficient to monitor the corneal surface. As shown in FIG. 14, an optical system imaging system 1402 is inserted between the mobile device 1401 and the eye 1404 to increase the spot density on the eye 1404. The system 1402 projects the diverging rays of the illumination pattern 1403 onto the eye and reimages it on the camera to reconstruct a high-resolution topography map. Due to sensitivity of infrared reflections to the tear film quality, and because video data is recorded by the camera, differential temporal analysis can be applied for tear film breakup analysis.

Robust Biometry

Optical biometry instruments today continue to have limitations in measuring ametropic, presbyopic, and emmetropic eyes alike, and the accuracy of the results is heavily dependent on patient fixation without a robust indicator for the accuracy of fixation at the time of the measurement. For example, the IOL Master 700 (Carl Zeiss Meditec) has a fixation verification feature that is not simultaneous to data acquisition. A-scan biometers measure the Axial Length (AL) by illuminating the cornea with a stationary and approximately collimated beam of light. They rely on eye alignment with respect to the biometer patient fixation to accomplish measurement of the axial length at the foveal pit. This approach works well only for properly-fixated emmetrpic eyes where the light beam is focused on the foveal pit plane. Ametropic and presbyopic eyes, broaden the beam to cover a wider region of the fovea resulting in blurring of the retinal signal in the axial dimension and less accurate reading in ametropic and presbyopic eyes. B-scan biometers utilize the same concept with the difference of a scanned rather than a stationary beam on the cornea. B-scan biometers suffer from the same beam focus challenge faced with A-scan biometers in ametropic and presbyopic eyes. Moreover, the paraxially-scanned beam on the anterior segment focuses results in pivoting of all beams on the foveal pit of the an emmetropic and fixated eye. For ametropic and presbyopic eyes, the pivot point will fall anterior or posterior to the foveal plane, causing additional blurring if one was to use information from all beams to calculate AL.

Figure 15:
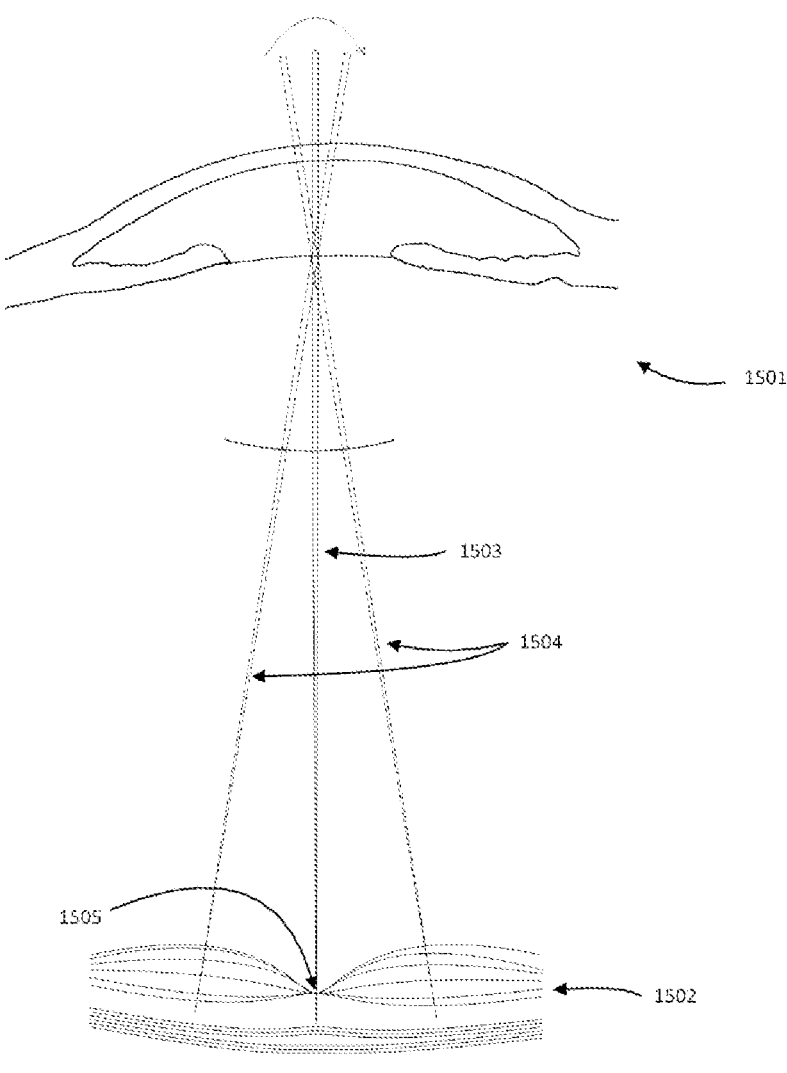
FIG. 15 shows a scan pattern that is preferably used for optical biometry where the beam is approximately focused on the retina and scanned around the pupil plane while OCT is imaging along the full-eye.

To overcome the issues of focus, blur, and fixation verification, FIG. 15 shows a scan pattern setup that is applied to the whole eye to generate accurate biometry information and fixation verification simultaneously. The beam 1503 is pivoted approximately in the pupil plane of the anterior segment 1501. In this case, the pupil plane is the plane in the anterior chamber of the eye that contains the pupil. Pupil center can be determined (for example, by camera imaging) and used as the pivot point. The marginal rays 1504 traverse an area on the retina 1502 while capturing the biometry information. The foveal pit 1505 can therefore be resolved clearly in the image. The beam enters the cornea with a wavefront that is preset to generate the focal point approximately on the RPE plane of the retina.

To enable this, the optical setup in the sample arm of the OCT system illuminates the eye with a converging scan beam, and to be able to adjust the pivot point to go around the pupil plane or behind it. In this example, the converging beams in the sample arm of the OCT system converge at the pivot point which can be at the pupil center, in the pupil plane or slightly anterior or posterior to the pupil plane.

The setup also contains focusing optics that adjusts to ensure that the beam is focused on the retina for ametropic, presbyopic, and emmetropic eyes alike This setup enables simultaneous visualization of all ocular surfaces required for biometry. The compromised lateral resolution at the anterior segment does not impact the accuracy for the basic measurements of Axial Length (AL), Anterior Chamber Depth (ACD), and Lens Thickness (T). Because the beam is focused on the retina and it traverses the retinal surface, it improves the consistency and accuracy of finding the Axial Length at the foveal pit. It also provides information about the fixation of the eye in the same image. This enables simultaneous fixation verification. It also enables finding critical biometry measurements (AL, ACD, and T) even for an unfixated eye.

Figure 16:
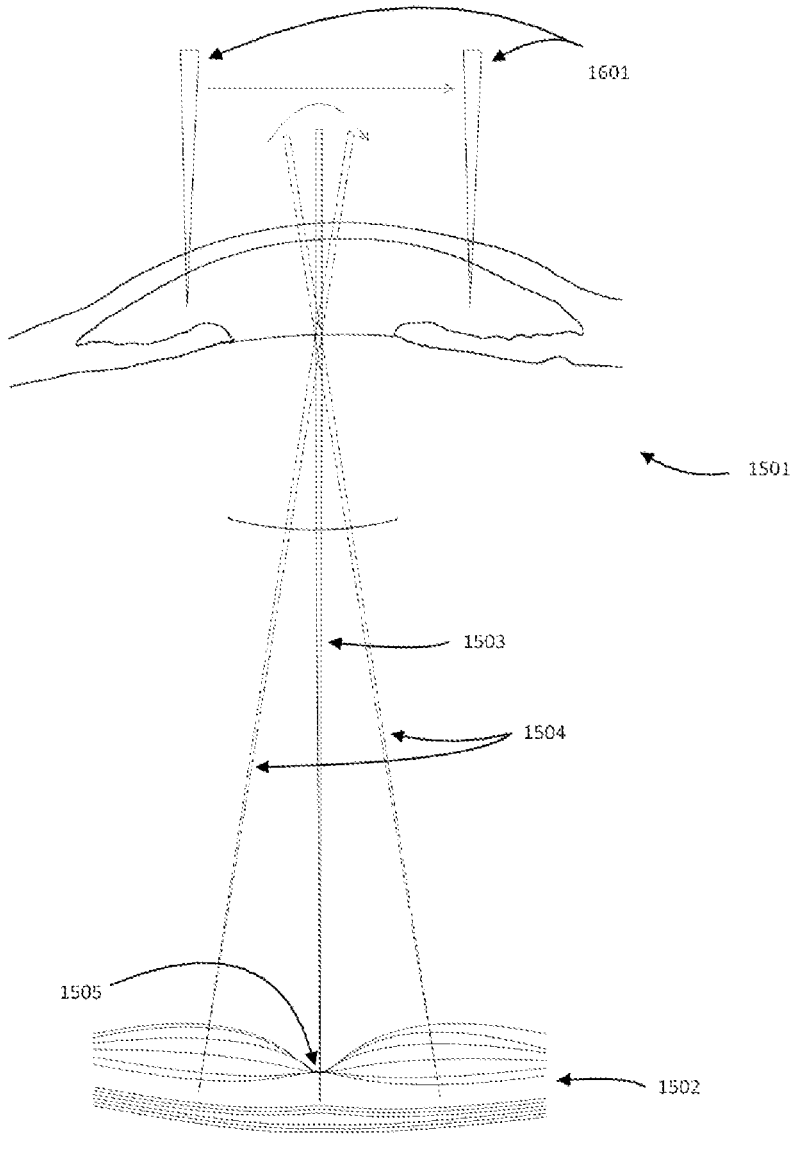
FIG. 16 shows a scan pattern that is preferably used for optical biometry where in one instance, the beam is approximately focused on the retina and scanned around the pupil plane while OCT is imaging along the full-eye, and in the other instances, the beam is approximately focused on the anterior segment and is and scanning along the anterior segment while OCT is imaging along part or the whole eye.

The configuration in FIG. 15 provides the ability to focus the beam on and scan it along the fovea. This provides advantages of accurate ranging of the foveal pit, and clear visualization to evaluate fixation. This configuration, however, compromises on the detailed view of the anterior segment. FIG. 16 shows the same system in FIG. 15 complemented with another scan arrangement 1601 that is approximately paraxial with an approximate focal plane within the anterior chamber. In the example of FIG. 16, the pivot point is moved away from the pupil to achieve scanning of the cornea, lens, iris, and the anterior chamber. Adding the paraxial scan enables achieving high-resolution image of the anterior segment that can be registered to the images recorded using the pivoting scan pattern. The registration of the two images or volumes provides a complete picture of the ocular surfaces with high resolution both in the anterior and posterior segments, without compromising on the accuracy of the biometry measurements achieved using the pivoting scan.

FIG. 17 shows arrangements that achieve the scan patterns described in FIG. 15 and FIG. 16. FIG. 17*a* shows an arrangement that does paraxial scanning of the eye. The OCT engine or A-line scanner 100 illuminates the collimator 1701 via the waveguide 1700. The collimated beam 1703 is scanned using the scanner mechanism 1702. The scanned beam 1704 is imaged using lenses 1705 and 1706. The phase or amplitude modulator 1707 is placed in the image plane of the scanner. The modulator is synched to the master trigger of 100 via the trigger line 1708. The scanned beam further propagates through the optical system comprised of lens 1709, delay element 1712, lenses 1710 and 1711 to illuminate the eye 1714 with a paraxially-scanned beam. The assembly 1713 comprised of lens 1710 and delay element 1712 is placed on a movable mechanism.

FIG. 17*b* shows the same arrangement in FIG. 17*a* where assembly 1713 is moved outside of the usable optical aperture. This results in a pivoting scan on the eye that is used to achieve the biometry scan show in FIG. 15 and FIG. 16.

The optical delay element 1712 eliminates or reduces the optical pathlength difference between the arrangements in FIG. 17*a* and FIG. 17*b*. The delay element 1712 can simply be a cube of glass. Preferably, delay element 1712 is comprised of an element with adjustable delay to account for different eye lengths. This can be achieved utilizing tilting of the optical cube to adjust the delay, or by using a wedge that can be moved to adjust the optical delay encountered by the beam. This preferred configuration enables switching between the two imaging modes with the same optical path delay.

It was described earlier that the beam may encounter optical focusing or defocusing as it propagates through the eye. This can be corrected by changing the power of the telescope comprised of lenses 1705 and 1706, the telescope comprised of lenses 1706 and 1709, or the telescope comprised of lenses 1709 and 1711. Any of these adjustments will requires adjustment of the scanning mechanism's drive signal to maintain the lateral imaging range.

FIGS. 17*c* and 17*d* show two settings of another arrangement that can be employed to achieve the pivoting and paraxial scans on the eye. FIG. 17*c* shows the OCT engine or A-line scanner 100 illuminating the scanning mechanism 1702 by the collimated beam propagated through the collimator 1701 and waveguide 1700. The scanned beam 1704 is modulated by the modulator 1707 which is synched to the OCT engine or A-line scanner 100 trigger via 1708. The telescope comprised of lenses 1705 and 1706 translates the beam to traverse the posterior segment of the eye 1714. The telescope is also used to achieve the desired focus on the retina. The lens 1706 is placed on a mechanism that removes or inserts it in the optical path. The assembly 1715 is movable in the axial dimension.

FIG. 17*d* shows the arrangement in FIG. 17*c* where the lens 1706 is removed from the optical path to accomplish a paraxial scan on the eye. The assembly 1715 is moved to adjust the optical pathlength of the sample arm. An additional optical delay such as delay element 1712 of FIG. 17*a* and FIG. 17*b* that works in tandem with lens 1706 can be employed in this arrangement as well.

What is claimed is:

1. An optical coherence tomography (OCT) system for providing accurate lateral mapping of images acquired via a scanning mechanism, the OCT system comprising:
    an A-line scanner subsystem comprising:
        a light source configured to output a light beam and an imaging engine clock to an object scanner subsystem;
        a detector configured to:
            capture an optical interference signal returned from the object scanner subsystem; and
            generate, based on the optical interference signal, an electrical signal; and
        one or more processors configured to:
            receive the electrical signal from the detector;
            process the electrical signal to form an uncorrected image comprising image elements and image markers;
            generate, based on the uncorrected image, a corrected image using the image elements and the image markers, wherein the corrected image is free from at least a portion of distortions present in the uncorrected image, and wherein the distortions are caused at least in part by scanning non-linearities associated with the object scanner subsystem; and
            provide mapping, imaging, and/or measurements of ocular surfaces; and
    the object scanner subsystem comprising:
        a scanner configured to direct the light beam towards an object via an optical path; and
        a modulator, located after the scanner along the optical path, wherein the modulator is configured to adjust the light beam towards the object in accordance with the imaging engine clock to generate the image markers, and wherein the modulator is triggered at a rate that produces the image markers on the image elements of the uncorrected image.

2. The OCT system of claim 1 wherein the A-line scanner subsystem comprises:
    a beam splitter and combiner configuration;
    a reference arrangement; and
    a sample scan arrangement.

3. The OCT system of claim 1, wherein the modulator causes a change of an image characteristic applicable to at least one image element, and the change to image elements includes one or more of: amplitude change, phase change, color change, speckle and/or speckle change.

4. The OCT system of claim 1, wherein the modulator is a passive modulator selected as an individual element or a combination incorporating spatial features that cause a change on phase, intensity, or another shift to an imaging event or more.

5. The OCT system of claim 1, wherein the one or more processors provide the mapping, imaging, and/or measurements of the ocular surfaces for IOL calculators or for planning of cataract and refractive surgeries.

* * * * *